United States Patent

Matsumoto et al.

[11] Patent Number: 5,608,132
[45] Date of Patent: Mar. 4, 1997

[54] METHOD OF ALKYLATING THE SIDE CHAIN OF ALKYL-SUBSTITUTED AROMATIC HYDROCARBONS

[75] Inventors: Takaya Matsumoto; Shinji Nishikawa; Fumio Kumata, all of Kanagawa, Japan

[73] Assignee: Mitsubishi Oil Co., Ltd., Tokyo, Japan

[21] Appl. No.: 417,964

[22] Filed: Apr. 6, 1995

[30] Foreign Application Priority Data

Apr. 14, 1994 [JP] Japan .................................. 6-099115

[51] Int. Cl.$^6$ ...................................................... C07C 2/72
[52] U.S. Cl. ........................... 585/452; 585/446; 585/453; 585/467
[58] Field of Search ........................... 585/446, 452, 585/453, 467; 502/341, 344

[56] References Cited

U.S. PATENT DOCUMENTS

| | | | |
|---|---|---|---|
| 4,034,052 | 7/1977 | Puskas | 585/438 |
| 4,656,156 | 4/1987 | Misra | 502/415 |
| 4,843,168 | 6/1989 | Drezdzon et al. | 585/440 |
| 4,970,191 | 11/1990 | Schutz | 502/341 |
| 5,227,559 | 7/1993 | Fukao et al. | 585/452 |
| 5,245,096 | 9/1993 | Derouane et al. | 585/419 |
| 5,276,233 | 1/1994 | Blom et al. | 585/419 |
| 5,354,932 | 10/1994 | Bhattacharyya et al. | 585/400 |

FOREIGN PATENT DOCUMENTS

| | | |
|---|---|---|
| 0128001 | 12/1984 | European Pat. Off. . |
| 0439679 | 8/1991 | European Pat. Off. . |
| 0644168 | 3/1995 | European Pat. Off. . |

*Primary Examiner*—Anthony R. McFarlane
*Assistant Examiner*—Walter D. Griffin
*Attorney, Agent, or Firm*—Sughrue, Mion, Zinn, Macpeak & Seas

[57] ABSTRACT

A method of alkylating a side chain of alkyl-substituted aromatic hydrocarbons. The method involves the steps of loading an alkali metal on a thermally treated hydrotalcite carrier represented by formula (I) by an impregnation method using the alkali metal dissolved in liquid ammonia, thermally treating the alkali metal loaded hydrotalcite carrier under vacuum to prepare a catalyst, then reacting an alkyl-substituted aromatic hydrocarbon with an aliphatic monoolefin using the catalyst under an atmosphere substantially free of oxygen, water and carbon dioxide gas to alkylate a side chain of the alkyl-substituted aromatic hydrocarbon:

$$[M^{2+}_{(1-x)} \cdot M^{3+}_{x}(OH)_2]^{x+} \cdot [A^{n-}_{x/n}]^{x-} \cdot yH_2O \qquad (I)$$

wherein $M^{2+}$ represents a divalent metallic cation, $M^{3+}$ represents a trivalent metallic cation, $A^{n-}$ represents an n-valent anion, n=0.1 to 0.5, x=0.1 to 0.5, and y=0 to 8.

14 Claims, No Drawings

METHOD OF ALKYLATING THE SIDE CHAIN OF ALKYL-SUBSTITUTED AROMATIC HYDROCARBONS

FIELD OF THE INVENTION

The present invention relates to a method of alkylating the side chain of alkyl-substituted aromatic hydrocarbons. More specifically, the present invention relates, for instance, to the economical production of 2-methyl-1-(p-tolyl)-butane by alkylation of the side chains of p-xylene with butene. By conducting a cyclic dehydration, the 2-methyl-1-(p-tolyl)-butane can form 2,6-dimethylnaphthalene, which is an industrially useful, polymerizable raw material. Thus, the present invention relates to an economical synthesis method for industrially useful, alkyl-substituted aromatic hydrocarbons.

BACKGROUND OF THE INVENTION

The alkylating reaction for the side chain(s) of alkyl-substituted aromatic hydrocarbons by aliphatic monoolefins is well known (e.g., see H. Pines 5, *J. Am. Chem. Soc.*, vol. 77 (1955)). However, this method is disadvantageous in that the sodium used cannot be recovered, and a large amount thereof is necessary since metallic sodium is directly added to the reaction solution and is used in a suspended state.

To avoid this disadvantage, a variety of methods have been proposed to load an alkali metal on a carrier for solidification. For example, U.K. Patent 1,269,280 and JP-A-61-221133 propose the use of potassium carbonate loaded sodium, JP-A-62-209027 proposes the use of potassium phosphate loaded sodium, JP-A-2-138229 (corresponding to U.S. Pat. No. 5,347,062) proposes the use of potassium hydroxide-alumina loaded potassium, JP-A-2-178236 (corresponding to U.S. Pat. No. 5,227,559) proposes the use of alumina loaded potassium, JP-A-3-264539 (U.S. Patent 5,118,895) proposes the use of magnesia loaded potassium, JP-A-3-227944 (U.S. Pat. No. 5,097,088) proposes the use of magnesia-alumina loaded potassium, etc. (The term "JP-A" as used herein means "unexamined published Japanese patent application".) In these documents, the use of aliphatic monoolefins such as ethylene, propylene and butene has been examined, and the reactivity decreases in the order of ethylene>propylene>butene. Thus, the reactivity of butene is lowest.

With respect to a conventional catalyst, a catalyst in which an alkali metal is loaded on a basic carrier has high activity, but it is disadvantageous in that the basic carrier has such a small specific area that the alkali metal loaded thereon is not sufficiently dispersed. On the other hand, an alumina catalyst in which an alkali metal is loaded on alumina has a high specific area and shows good dispersibility for the loaded metal. However, because of the acidic nature of alumina, such an alumina catalyst cannot provide sufficient activity for alkylating side chains if it is produced by conventional catalyst production methods.

SUMMARY OF THE INVENTION

An object of the present invention is to provide a novel method of alkylating the side chain of alkyl-substituted aromatic hydrocarbons with an aliphatic monoolefin(s). In particular, the present invention relates to a novel method which efficiently enables one to synthesize 2-methyl-1-(p-tolyl)-butane by causing the side chain alkylation of p-xylene, at a high conversion rate, using low reactive butene as a raw material.

The reaction system of the present invention potentially entails some side reactions such as the formation of a butene dimer by reaction between butenes and alkylation of a benzene ring by reaction between p-xylene and butene, etc.

Thus, another object of the present invention is to prevent such side reactions from occurring and to insure they are kept as low as possible. In order to inhibit the dimerization of butene, it is effective, for instance, to lower the reaction temperature and the reactant concentration, which requires developing a catalyst having a sufficient activity at a low temperature or at a low reactant concentration. In order to inhibit the alkylation of a benzene ring, it is necessary to decrease the acidity of a catalyst carrier, which is accomplished by loading an alkali amide such as sodium amide and potassium amide.

As a result of intensive research to develop a method of reacting aliphatic monoolefins, especially low reactive butene, the present inventors found that 2-methyl-1-(p-tolyl)-butane can be formed at a high conversion rate and at high selectivity by a method which involves the use of a catalyst in which an alkali metal dissolved in liquid ammonia is loaded on a hydrotalcite carrier having a high specific area (e.g., 50 to 400 m$^2$/g). Loading is by an impregnation method and is followed by conducting the alkylation reaction in an atmosphere substantially free from oxygen, water and carbon dioxide gas.

More specifically, the present invention involves a method of alkylating the side chain of alkyl-substituted aromatic hydrocarbons, which comprises loading an alkali metal on a thermally treated hydrotalcite carrier represented by formula (I) by an impregnation method where the alkali metal is contacted with the thermally treated hydrotalcite while the alkali metal is dissolved in liquid ammonia. The alkali metal loaded hydrotalcite carrier is then thermally treated under vacuum to prepare a catalyst. An alkyl-substituted aromatic hydrocarbon is then reacted with an aliphatic monoolefin using the catalyst under an atmosphere substantially free of oxygen, water and carbon dioxide gas to alkylate the side chain of the alkyl-substituted aromatic hydrocarbon:

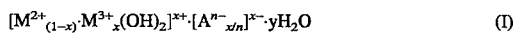

$$[M^{2+}{}_{(1-x)} \cdot M^{3+}{}_x (OH)_2]^{x+} \cdot [A^{n-}{}_{x/n}]^{x-} \cdot y H_2 O \qquad (I)$$

wherein $M^{2+}$ represents a divalent metallic cation, $M^{3+}$ represents a trivalent metallic cation, $A^{n-}$ represents an n-valent anion, n=0.1 to 0.5, x=0.1 to 0.5 and y=0 to 8.

DETAILED DESCRIPTION OF THE INVENTION

Alkyl-substituted aromatic hydrocarbons such as toluene, xylene, ethylbenzene, trimethylbenzene, methylnaphthalene and the like will undergo a similar side chain alkylation reaction. In the case of producing 2-methyl-1-(p-tolyl)-butane, which is useful as a polymerizable raw material, p-xylene is preferably used as a reactant. In this case, as a raw p-xylene material, it is desirable impurities be present in as small an amount as possible, and it is preferable for the p-xylene to have a purity of 99.5% or more. One of the impurities present therein is ethylbenzene whose boiling point is very close to that of p-xylene. In addition, other impurities include a small amount of water, oxygen and carbon dioxide gas. Since this small amount of impurities adversely affects the catalyst, it is preferable to limit the water content to 1 ppm or less, the oxygen content to 10 ppm or less, and the carbon dioxide content to 1 ppm or less.

In a preferred embodiment, the alkyl-substituted aromatic hydrocarbon is a mono-cyclic aromatic group in which the number of the side chain alkyl group is 1 or 2 and the carbon number of the side chain alkyl group is 1.

Aliphatic monoolefins such as ethylene, propylene, butene, heptene and the like undergo a similar reaction. In the case of producing 2-methyl-1-(p-tolyl)-butane, butene is preferably used. Though the term butene includes 1-butene or 2-butene, each butene can be used since each one undergoes the same reaction. The reason for this is that when the catalyst of the present invention is used, the isomerization of butene proceeds very rapidly, and one reaches an equilibrium composition quickly. As the source of the raw material butene, it is typical to use a product obtained by the thermal cracking or the catalytic cracking of petroleum, though this is not essential and any butene produced by any process can be used. However, it is preferable to limit the water content to 1 ppm or less, the oxygen content to 10 ppm or less, and the carbon dioxide content to 1 ppm or less, as in the case of p-xylene, which is also applicable to the other raw materials. With respect to the other impurities, in general, an acidic substance (not only carbon dioxide, but also inclusive of other substances) catalytically poisons a basic catalyst, then it is preferable to completely remove it as possible.

In a preferred embodiment, the aliphatic monoolefin contains 2 to 5 carbon atoms.

The catalyst for use in the present invention can be prepared as follows:

As shown by the composition $Mg_6Al_2(OH)_{16}CO_3 \cdot 4H_2O$ which is a typical hydrotalcite compound, hydrotalcite is a compound in which a part of the divalent Mg ion present is substituted with trivalent Al ion. Also, $Mg_6Fe_2(OH)_{16}(CO_3^{2-}) \cdot 4H_2O$ and $Ni_6Fe_2(OH)_{16}(CO_3^{2-}) \cdot 4H_2O$ are typical hydrotalcite compounds. In general, a hydrotalcite is represented by the following formula (I):

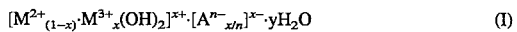

$$[M^{2+}_{(1-x)} \cdot M^{3+}_x (OH)_2]^{x+} \cdot [A^{n-}_{x/n}]^{x-} \cdot yH_2O \qquad (I)$$

$M^{2+}$ is a divalent metallic cation. In naturally occurring hydrotalcite, $Mg^{2+}$, $Ni^{2+}$, $Zn^{2+}$, etc., occur as $M^{2+}$. In synthetically prepared hydrotalcite, $Mg^{2+}$, $Ni^{2+}$, $Co^{2+}$, $Zn^{2+}$, etc., prepared as $M^{2+}$.

$M^{3+}$ is a trivalent cation, including, e.g., $Al^{3+}$, $Cr^{3+}$, $Mn^{3+}$, $Fe^{3+}$.

$A^{n-}$ is an n-valent anion, and it is usually $CO_3^{2-}$.

The range of x is from about 0.2 to 0.3 in naturally occurring hydrotalcite. In synthetically produced hydrotalcite, the range of from about 0.09 to 0.5 has been attempted.

The range of y varies depending on the ratio of the divalent/trivalent metallic cation ratio and the drying conditions, but it usually ranges from about 0 to 8.

The synthesis of a hydrotalcite is described, for example, in *Journal of Catalyst,* vol. 94, page 547 and vol. 101, page 352. The hydrotalcite has a layer structure comprising a basic layer which is positively charged having a structure similar to brucite ($Mg(OH_2)$) and an interlayer which is negatively charged having an anion such as $CO_3^{2-}$ and intercalation water.

When a hydrotalcite is heated, intercalation water in an interlayer is eliminated and the intercalation water is completely evaporated up to 300° C. When the temperature is subsequently elevated, while any hydroxyl group(s) bonded to metallic ion is/are dehydrated by condensation, $CO_3^{2-}$ is eliminated as $CO_2$. As the water content and the carbonic acid gas are eliminated, the surface area and tile pore volume are increased, becoming nearly constant at about 500° C.

Even with this thermal treatment, the crystalline state and the layer structure of the hydrotalcite remain without being destroyed, and they remain essentially stable up to a temperature of 700° C. When heated higher than 700° C., the layer structure is destroyed. Accordingly, a suitable heating temperature is from 300° to 700° C., more preferable from 300° to 600° C. For dehydration and decarboxylation to sufficiently proceed, a suitable calcination time is from 1 to 50 hours, more preferably from 2 to 30 hours, and the calcination is conducted under atmospheric pressure in an air atmosphere.

After heating, the hydrotalcite is cooled to room temperature, and then an alkali metal is added thereto in an inert gas atmosphere (e.g., helium, argon, xenon) by introducing an inert gas such as helium gas or nitrogen gas. The amount of alkali metal added is 0.5 to 40 wt %, preferably 2 to 30 wt %, based on the amount (weight) of the hydrotalcite carrier. After addition of the alkali metal, the resulting product is cooled to −33° C. (which is the boiling point of ammonia) or lower (usually, −33° C. to −70° C.), under reduced pressure (usually, 750 to 500 mmHg abs.). Thus, when ammonia gas is introduced (e.g., 5 to 100 times the amount of the alkali metal), the ammonia becomes liquid, i.e., undergoes a phase change to liquid ammonia. An alkali metal is highly soluble in liquid ammonia. After the alkali metal is dissolved, the system is allowed to stand for a while (e.g., 30 minutes to 10 hours) so that it reaches room temperature, and then ammonia gas is exhausted therefrom. As alkali metals, sodium or potassium are preferred.

After exhausting ammonia gas, the system is further thermally treated under vacuum (e.g., 100 to $10^{-5}$ mmHg abs.). The thermal treatment is conducted at 100° to 500° C., preferably at 200° to 400° C. for 10 minutes to 10 hours, preferably at 1 to 5 hours.

In the present invention, the catalyst size is preferably 80 to 200 mesh.

The catalyst thus prepared is used to effect reaction. The reaction can be conducted as either a batch process or a continuous process. In a laboratory, it is convenient to use a batch process. Industrially, it is preferred to use a continuous process.

In a batch process, the catalyst thus prepared is placed in a reactor, in an inert gas atmosphere, and then the reactor is charged with a purified alkyl-substituted aromatic hydrocarbon. After the system is elevated to the reaction temperature, an aliphatic monoolefin is added.

In a batch process, the amount of catalyst is in the range of 0.1 to 20 wt %, preferably 2 to 10 wt %, based on the amount of alkyl-substituted aromatic hydrocarbon. However, the amount of catalyst may vary depending on the alkali metal loading amount, the reaction temperature, and the reaction time. Generally, from the thermodynamic equilibrium standpoint, it is advantageous to apply a lower reaction temperature, but from the reaction kinetics standpoint, it is advantageous to apply a higher temperature. Usually, the reaction is conducted at 100 to 400° C., preferably at 150° to 300° C., for 1 to 20 hours, preferably 2 to 10 hours. Also, from the thermodynamic equilibrium standpoint, it is advantageous to use a higher pressure, but a pressurizing energy is required for a higher pressure and requires an expensive device. Usually, the reaction is conducted at a pressure of 5 to 100 kg/cm², preferably 20 to 80 kg/cm².

Examples of a continuous process include, for example, a fixed bed flow reactor, a fluidized bed reactor, a continuous batch reactor, etc. In addition, examples thereof include various types of reactors, such as a fixed bed reaction distillation type reactor and a boiling bed reactor. Any of these reactors are useful. The reaction conditions in the continuous process are similar to those in the batch process, since the reaction involved does not change.

The present invention will now be illustrated in greater detail with reference to the following Examples, but the present invention should not be construed as being limited thereto. Unless otherwise indicated herein, all parts, percents, ratios and the like are by weight. Also, unless otherwise indicated, all operations is conducted by atmospheric pressure.

EXAMPLE 1

(1) Preparation of Catalyst 52 g of sodium hydroxide and 5.3 g of sodium carbonate anhydride were dissolved in 240 ml of water, and the product was designated Solution A. 128.2 g of magnesium nitrate and 37.5 g of aluminum nitrate were dissolved in 600 ml of water, and the product was designated Solution B. Solution B was dropwise added to Solution A at room temperature over a period of 1 hour while stirring Solution A. After the dropwise addition, the resulting mixture was heated to 65° C. and reacted at 65° C. with stirring for 16 hours. After reaction, the temperature was decreased to room temperature and then the solid content in the resulting solution was filtered out. The filtered solid content was washed with distilled water several times, and dried at 125° C. for 12 hours in air. 15.8 g of the solid powder thus obtained was calcined at 450° C. for 10 hours in air. After calcination, inert nitrogen gas was introduced to blanket the solid powder. Then, the system was allowed to reach atmospheric pressure, and the temperature was decreased to room temperature. After reaching room temperature, 2.0 g of metallic sodium was added thereto while passing nitrogen gas through the system. The mixture of metallic sodium and hydrotalcite was cooled to a temperature range of −33° C. to −70° C. with a dry ice—methanol solution, and then the system degassed under a vacuum pressure range of 750 to 500 mmHg abs. Ammonia gas was then added and the ammonia gas liquified at the temperature of the system. After the system was allowed to stand for 1 hour at a temperature range of −33° C. to −70° C., it was gradually elevated to room temperature. The vaporized ammonia generated was removed by evacuation. The system was then elevated to 300° C., and the system was maintained for 3 hours at 300° C. Thereafter, the system was cooled to room temperature and the product was stored in nitrogen gas. The catalyst thus obtained was designated as Catalyst A.

(2) Synthesis Reaction of 2-Methyl-1-(p-Tolyl)-Butane 50 ml of purified p-xylene having a purity of 99.8% and 5 g of Catalyst A were added to a reactor having an inner volume of 150 ml. After being blanketed with a nitrogen atmosphere, the system was elevated to 180° C. After reaching 180° C., 9.8 g of butene was poured into the mixture, and the reaction was conducted under 20 kg/cm² g for 3 hours at 180° C.

EXAMPLE 2

Catalyst B was prepared in the same manner as in Example 1, except that 2.0 g of metallic potassium was added instead of 2.0 g of metallic sodium. Then, a Synthesis Reaction was conducted in the same manner as in Example 1, except for the use of Catalyst B instead of Catalyst A.

EXAMPLE 3

Catalyst C was prepared in the same manner as in Example 1, except that 0.5 g of metallic sodium was used. Then, a Synthesis Reaction was conducted in the same manner as in Example 1, except that Catalyst C was used instead of Catalyst A, the reaction temperature changed to 250° C., and the reaction time was changed to 5 hours.

EXAMPLE 4

Catalyst D was prepared in the same manner as in Example 1, except that 76.9 g of magnesium nitrate was used instead of 128.2 g of magnesium nitrate and 0.5 g of metallic potassium was used instead of 2.0 g of metallic sodium. Then, a Synthesis Reaction was conducted in the same manner as in Example 1, except that Catalyst D was used instead of Catalyst A, the reaction temperature was changed to 275° C., and the reaction time was changed to 10 hours.

Comparative Example 1

Catalyst E was prepared in the same manner as in Example 1, except that the temperature elevation was not conducted after the ammonia evacuation. Then, a Synthesis Reaction was conducted in the same manner as in Example 1, except for the use of Catalyst E instead of Catalyst A.

The results obtained are shown in Table 1 below.

TABLE 1

Results of Synthesis Reaction of
2-Methyl-1-(p-Tolyl)-Butene (2MTB)

| | Catalyst | p-Xylene Conversion (%) | Butene Conversion (%) | 2MTB Yield (%) | 2MTB Selectivity (%) |
|---|---|---|---|---|---|
| Example 1 | A | 24 | 65 | 17 | 71 |
| Example 2 | B | 19 | 62 | 14 | 74 |
| Example 3 | C | 32 | 91 | 26 | 81 |
| Example 4 | D | 44 | 97 | 32 | 71 |
| Com. Ex. 1 | E | 1.6 | 3.1 | 0.8 | 50 |

Note: 2MTB Selectivity = (2MTB Yield/p-Xylene Conversion) × 100

From the results in Table 1 above, it is apparent that a catalyst which was prepared by not conducting a temperature elevation after the ammonia evacuation (Catalyst E) was remarkably inferior in activity as compared to the catalysts of the present invention.

As described above, the present invention makes it possible to alkylate the side chains of p-xylene using butene, at a high conversion rate, which has been conventionally considered to be difficult. Moreover, the present invention also makes it possible to obtain 2-methyl-1-(p-tolyl)-butane at high selectivity. Previous methods utilized to obtain this compound have been quite expensive. By the cyclical dehydration of the compound using conventional techniques, the present invention makes it possible to economically produce 2,6-dimethylnaphthalene as a raw material for producing a useful high molecular weight material such as polyester fibers and plastics.

While the invention has been described in detail and with reference to specific examples thereof, it will be apparent to one of ordinary skill in the art that various changes and modifications can be made herein without departing from the spirit and scope of the invention.

What is claimed is:

1. A method of alkylating a side chain of an alkyl-substituted aromatic hydrocarbon, comprising the steps of:

(A) thermally treating a hydrotalcite carrier represented by the following formula (I):

$$[M^{2+}_{(1-x)} \cdot M^{3+}_{x}(OH)_2]^{x+} \cdot [A^{n-}_{x/n}]^{x-} \cdot yH_2O \quad \text{(I)}$$

wherein $M^{2+}$ represents a divalent metallic cation, $M^{3+}$ represents a trivalent metallic cation, $A^{n-}$ represents an n-valent anion, n=0.1 to 0.5, x=0.1 to 0.5, and y=0 to 8, so as to prepare a thermally treated hydrotalcite carrier;

(B) loading an alkali metal on the thermally treated hydrotalcite carrier of step (A) by an impregnation method, wherein the alkali metal is contacted with the thermally treated hydrotalcite carrier while the alkali metal is dissolved in liquid ammonia, so as to prepare an alkali metal loaded hydrotalcite carrier;

(C) thermally treating the alkali metal loaded hydrotalcite carrier of step (B) under vacuum so as to prepare a catalyst; and (D) reacting an alkyl-substituted aromatic hydrocarbon with an aliphatic monoolefin using the catalyst of step (C) under an atmosphere substantially free of oxygen, water and carbon dioxide gas so as to alkylate a side chain of the alkyl-substituted aromatic hydrocarbon.

2. The method of claim 1, wherein the alkyl-substituted aromatic hydrocarbon is p-xylene.

3. The method of claim 1, wherein the aliphatic monoolefin is 1-butene or 2-butene.

4. The method of claim 2, wherein the aliphatic monoolefin is 1-butene or 2-butene.

5. The method of claim 1, wherein the alkali metal is sodium or potassium.

6. The method of claims 1, wherein in the hydrotalcite represented by formula (I), $M^{2+}$ is $Mg^{2+}$, $M^{3+}$ is $Al^{3+}$, x is from 0.1 to 0.5, and $A^{n-}$ is $CO_3^{2-}$.

7. The method of claim 1, wherein the hydrotalcite carrier of step (A) is thermally treated at 300° to 700° C. for 1 to 50 hours.

8. The method of claim 7, wherein the hydrotalcite carrier of step (A) is thermally treated at 300° to 600° C. for 2 to 30 hours.

9. The method of claim 1, wherein the alkali metal is loaded in an amount of 0.5 to 40% by weight based on the amount of the thermally treated hydrotalcite carrier of step (A).

10. The method of claim 9, wherein the alkali metal is loaded in an amount of 2 to 30% by weight based on the amount of the thermally treated hydrotalcite carrier of step (A).

11. The method of claim 1, wherein the alkali metal loaded hydrotalcite carrier of step (C), is thermally treated at 100° to 500° C. for 10 minutes to 10 hours to prepare a catalyst.

12. The method of claim 11, wherein the alkali metal loaded hydrotalcite carrier of step (C), is thermally treated at 200° to 400° C. for 1 to 5 hours under vacuum to prepare a catalyst.

13. The method of claim 1, wherein the alkylation of the side chain of the alkyl-substituted aromatic hydrocarbon in step (D) is conducted at 100° to 400° C. for 1 to 20 hours.

14. The method of claim 13, wherein the alkylation of the side chain of the alkyl-substituted aromatic hydrocarbon is conducted at 150° to 300° C. for 2 to 10 hours.

* * * * *